(12) United States Patent
Bennett

(10) Patent No.: US 6,635,037 B1
(45) Date of Patent: Oct. 21, 2003

(54) MALE URINARY INCONTINENCE DEVICE

(76) Inventor: Patricia A. Bennett, 1300 J.E. Woody Rd, Springtown, TX (US) 76082

( * ) Notice: Subject to any disclaimer, the term of this patent is extended or adjusted under 35 U.S.C. 154(b) by 0 days.

(21) Appl. No.: 09/838,783

(22) Filed: Apr. 20, 2001

Related U.S. Application Data

(60) Provisional application No. 60/258,936, filed on Dec. 29, 2000.

(51) Int. Cl.$^7$ .................................................. A61F 5/44
(52) U.S. Cl. ....................................... 604/349; 604/353
(58) Field of Search ............................ 604/544, 322, 604/326, 327, 346–354

(56) References Cited

U.S. PATENT DOCUMENTS

| | | | |
|---|---|---|---|
| 3,742,953 A | | 7/1973 | Lee .............................. 128/295 |
| 3,749,096 A | * | 7/1973 | Donaldson ................. 604/351 |
| 4,022,213 A | | 5/1977 | Stein ......................... 604/350 |
| 4,387,726 A | | 6/1983 | Denard ........................ 128/760 |
| 4,568,340 A | * | 2/1986 | Giacalone ...................... 2/405 |
| 4,813,935 A | | 3/1989 | Haber et al. .................. 604/99 |
| 5,013,308 A | * | 5/1991 | Sullivan et al. ............. 604/349 |
| 5,184,629 A | | 2/1993 | Erickson et al. ............ 128/885 |
| 5,346,483 A | * | 9/1994 | Thaxton, Sr. ................ 600/580 |
| 5,423,785 A | * | 6/1995 | Hart ............................ 604/317 |
| 5,531,725 A | | 7/1996 | Steer ........................... 604/349 |
| 5,727,568 A | | 3/1998 | Kiser .......................... 128/885 |
| 6,007,526 A | | 12/1999 | Passalaqua et al. ......... 604/349 |
| 6,110,099 A | | 8/2000 | Benderev ..................... 600/30 |
| 6,248,096 B1 | * | 6/2001 | Dwork et al. ............... 604/347 |

* cited by examiner

*Primary Examiner*—Weilun Lo
*Assistant Examiner*—C. Lynne Anderson
(74) *Attorney, Agent, or Firm*—James E. Walton; Hill & Hunn, LLP

(57) ABSTRACT

The present invention is a male urinary incontinence management device comprising a base support portion, an external condom catheter portion, and an adjustable strap portion. The base support portion has a periphery of generally uniform thickness, a concave rear surface, a stiffened central support portion, and an aperture which passes through the central portion. The external condom catheter portion is attached to the base support portion and is in fluid communication with the aperture. An adjustment means is carried by the base support portion. The adjustable strap portion releasably and adjustably attaches to the base support portion at the adjustment means. The base support portion can be used with either conventional external condom catheters or external condom catheters according to the present invention.

18 Claims, 4 Drawing Sheets

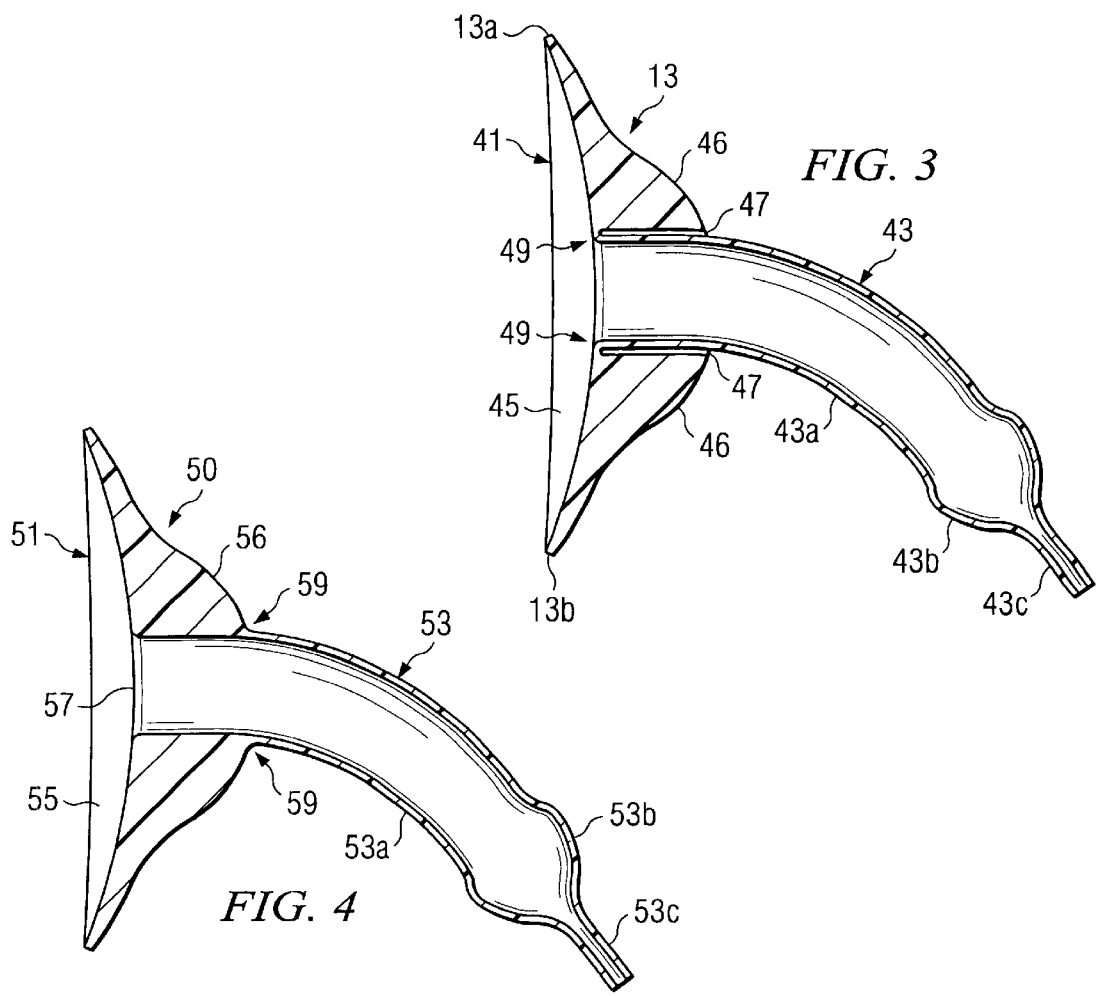
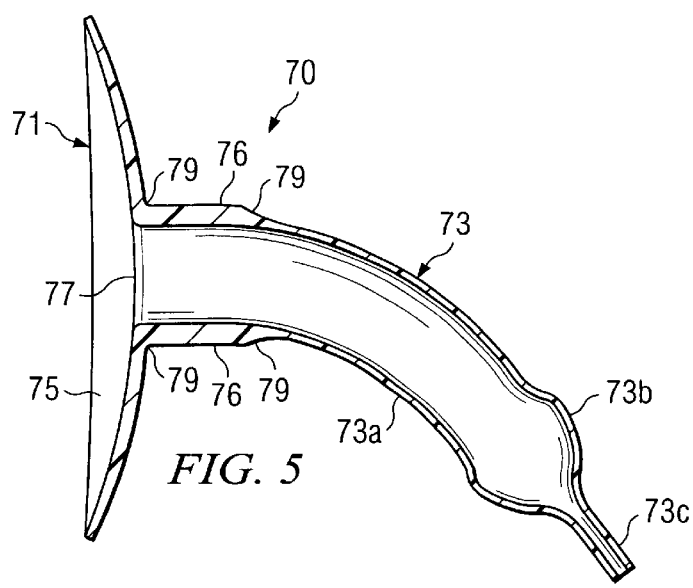

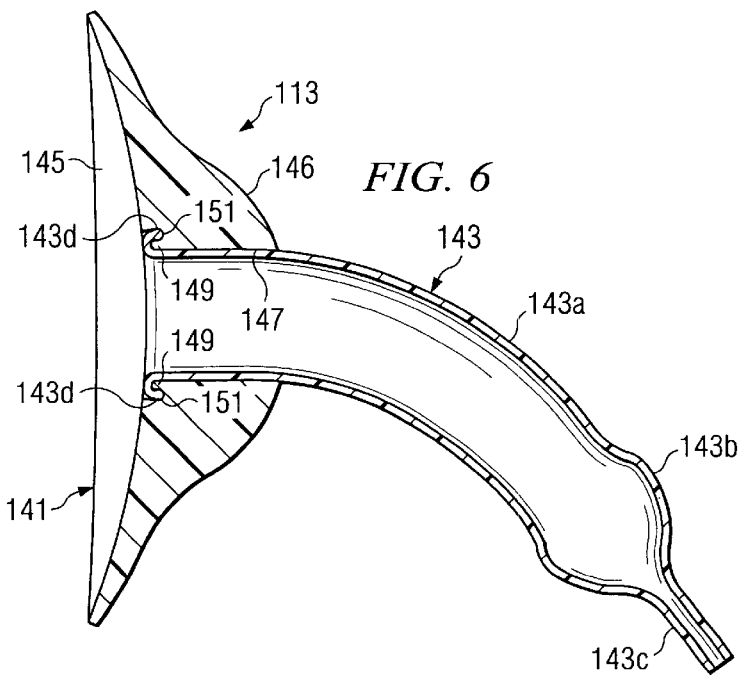
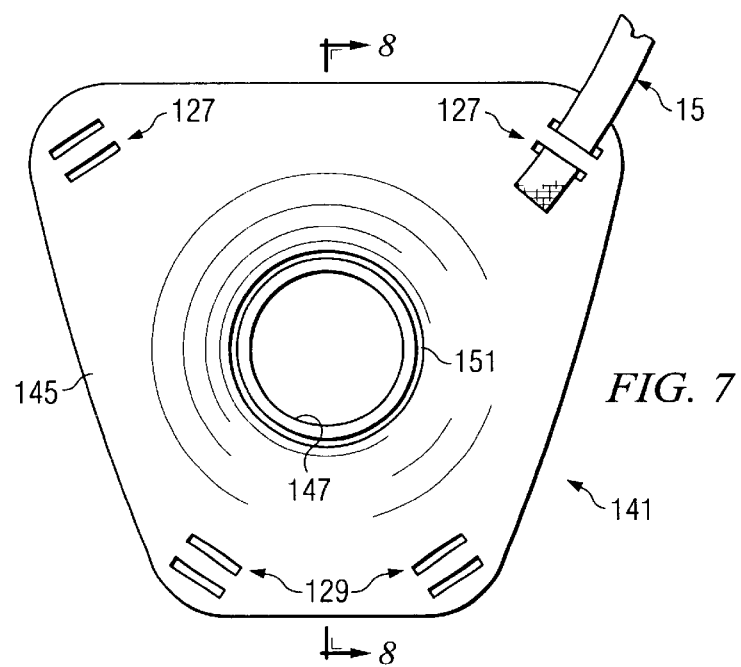

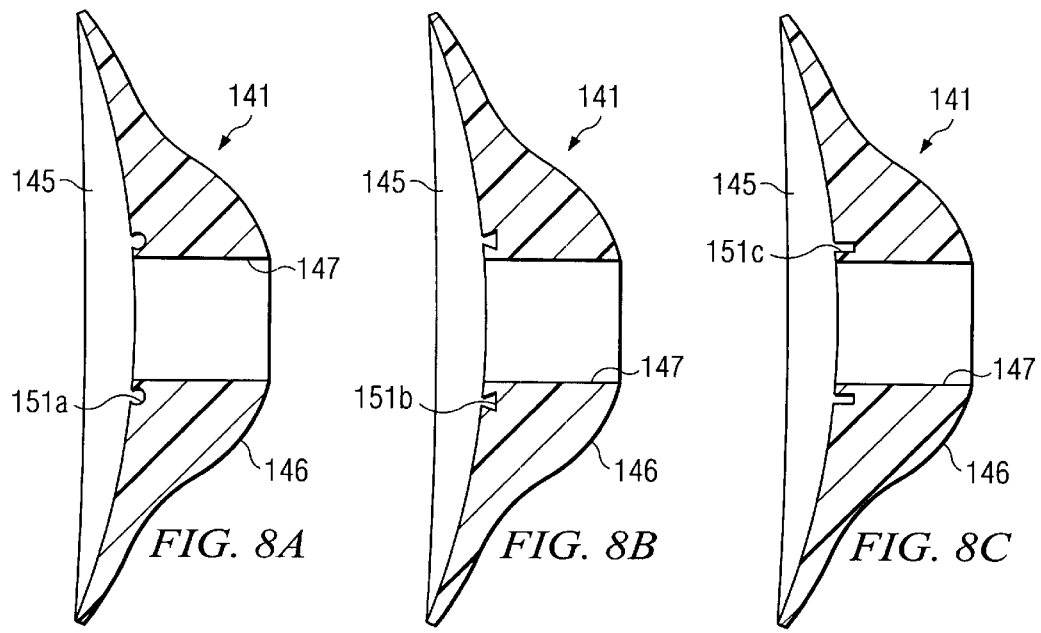
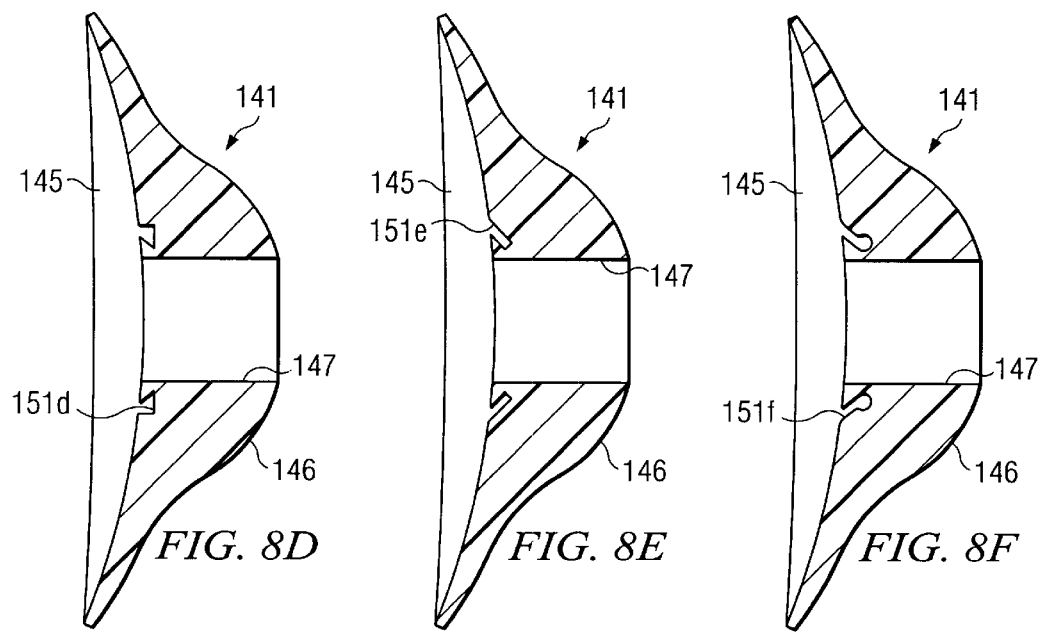

MALE URINARY INCONTINENCE DEVICE

This application claims the benefit of U.S. Provisional Application No. 60/258,936, filed Dec. 29, 2000, titled "Male Urinary Incontinence Device."

BACKGROUND ART

1. Field of the Invention

The present invention relates to urinary incontinence devices. In particular, the present invention relates to devices for managing male urinary incontinence.

2. Description of Related Art

Urinary incontinence is believed to affect 15% to 30% of non-institutionalized people over the age of 60, and over 50% of the people in convalescent and nursing homes. Treatment for urinary incontinence generally falls into the following categories: (1) management devices, which either restrict the flow of urine, or simply redirect and retain the urine; (2) behavioral treatment, which involves bladder re-training by voiding on a timed schedule or the performance of exercises to strengthen pelvic muscles; (3) pharmacological treatment, which involves the long-term use of drugs; and (4) surgical treatment, which involves the performance of major surgery while the patient is under anesthesia. Although each of these categories of treatment offer some measure of relief, each has significant side effects. The present invention relates to the management of male urinary incontinence.

There are many male urinary incontinence management devices on the market at this time, ranging from the most intrusive: urinary tract catheters; to the least intrusive: diapers. Neither of these devices, nor anything in between, offer the safe, comfortable, and non-traumatic control or management of male urinary incontinence. Although urinary tract catheters, such as Foley catheters, are often necessary, their intrusive nature often leads to urinary tract infections. In addition, the insertion and extraction of Foley catheters are quite traumatic for the patient. On the other hand, although diapers are quick and easy to use, they often lead to skin breakdown, and are virtually useless when it is necessary to maintain an accurate measure of a patient's fluid intake and output.

The following U.S. patents represent attempts to manage male urinary incontinence with the use of external condom-type catheters: U.S. Pat. No. 6,007,526 issued to Passalaqua et al., which discloses an external catheter having a sealing flap; U.S. Pat. No. 5,531,725 issued to Steer, which discloses an external condom catheter that is adhered by an internal adhesive strip to the penis; U.S. Pat. No. 4,387,726 issued to Denard, which discloses a dual-container, urine collection device; and U.S. Pat. No. 3,742,953 issued to Lee, which discloses an external condom catheter having a resilient element for retaining the device on the penis. In practice, these devices lack the necessary base support to prevent them from falling off of the penis, particularly when the penis is inverted.

BRIEF SUMMARY OF THE INVENTION

There is a need for a male urinary incontinence management device that is non-intrusive and that has means for securing the device to the penis.

Therefore, it is an object of the present invention to provide a male urinary incontinence management device that is non-intrusive and that has means for securing the device to the penis.

The above objects are achieved by providing a male urinary incontinence management device having a base support member, an external condom catheter coupled to the base support member, and an adjustable strap system to prevent the device from falling off of the penis.

The present invention has significant advantages, including: (1) it prevents skin breakdown, because urine is prevented from remaining in contact with the skin; (2) it prevents urinary tract infections, because the device is non-intrusive; (3) it improves patient comfort, because the device does not excessively compress the penis or restrict urine flow; (4) it allows accurate measuring of output of fluids without internal catheterization; and (5) it reduces the number linen changes, resulting in savings in time, cost, and labor.

The above objects and advantages, as well as others, will be evident from the following detailed description of the present invention.

BRIEF DESCRIPTION OF THE DRAWINGS

FIG. 3 is a cross-sectional view of the device of FIG. 1 taken at III—III in FIG. 2.

FIG. 4 is an alternate embodiment of the male urinary incontinence management device of FIG. 1.

FIG. 5 is an another alternate embodiment of the male urinary incontinence management device of FIG. 1.

FIG. 6 is a cross-sectional view of an alternate embodiment of the male urinary incontinence management device according to the present invention.

FIG. 7 is a rear plan view of the base support portion of the male urinary incontinence management device of FIG. 6.

FIGS. 8A–8F are cross-sectional views taken along VIII—VIII of FIG. 7 illustrating various embodiments of the condom catheter retaining means of the base support portion of the male urinary incontinence management device of FIG. 6.

DETAILED DESCRIPTION OF THE PREFERRED EMBODIMENT

Figure 1:
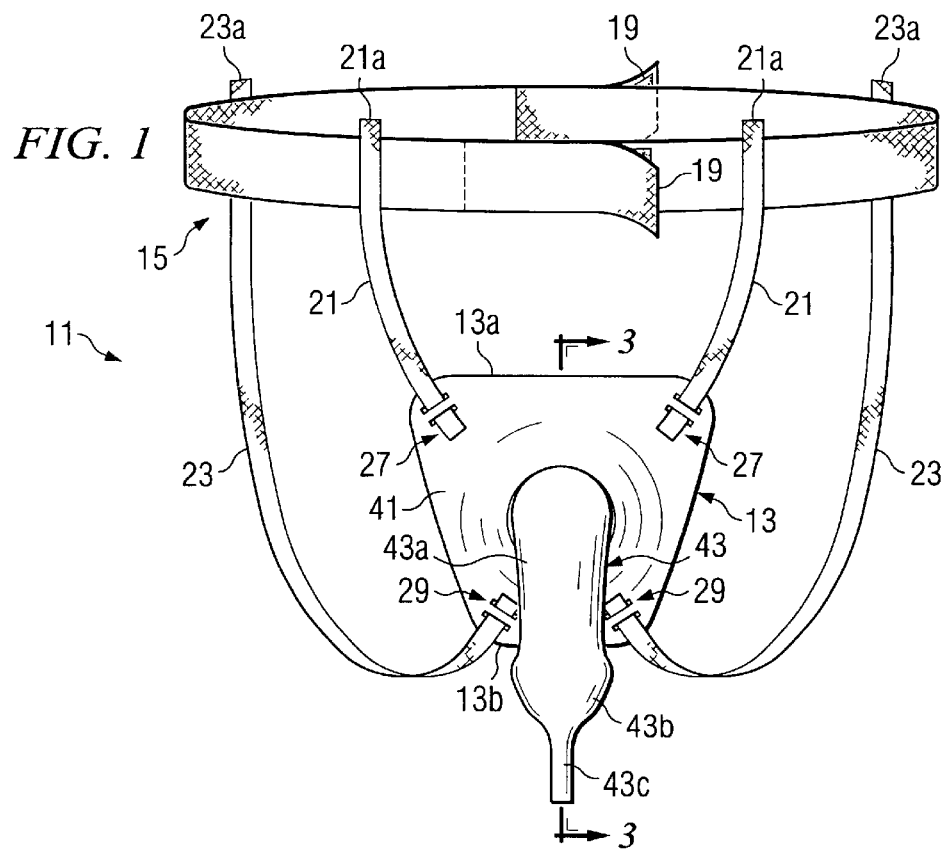
FIG. 1 is a front view of the male urinary incontinence management device according to the present invention.
Figure 2:
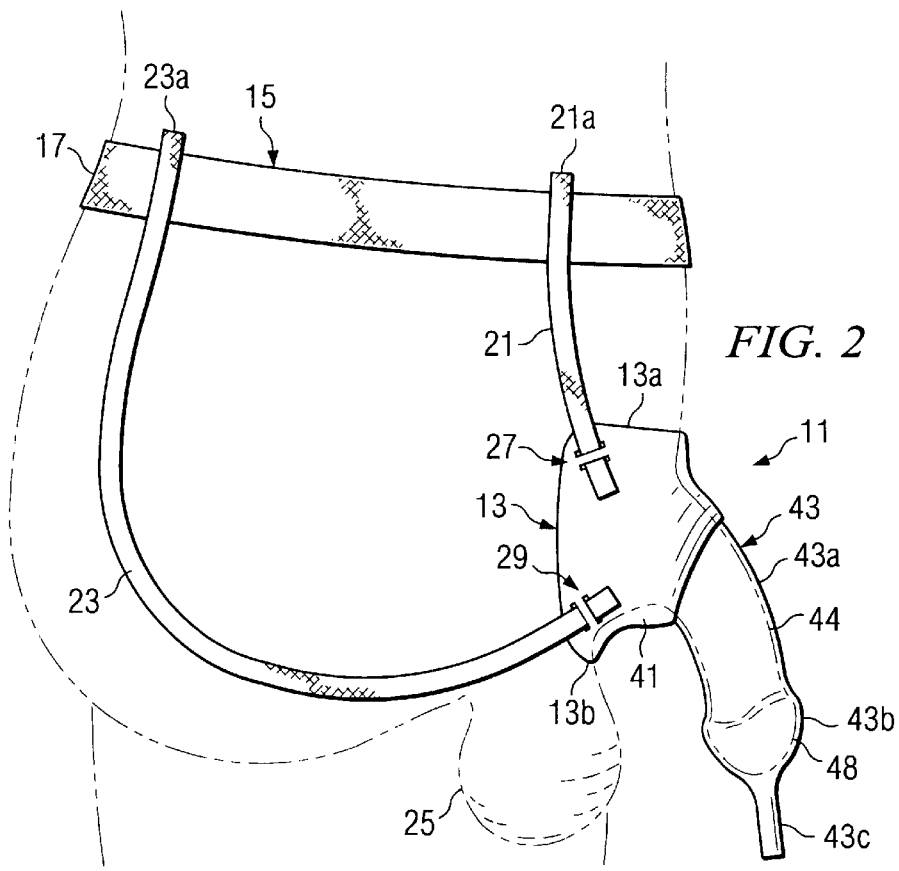
FIG. 2 is a side view of the device of FIG. 1 applied to a male patient.

Referring to FIGS. 1 and 2 in the drawings, the preferred embodiment of a male urinary incontinence management device 11 according to the present invention is illustrated. Device 11 includes an external catheter portion 13 and a strap portion 15. Strap portion 15 includes an adjustable waistband 17, at least one conventional waistband adjustment means 19, at least one frontal extension band 21, and at least one rear extension band 23. Waistband adjustment means 19 is preferably hook and loop tape, but may include tape, hooks, loops, buttons, or snaps. In addition, waistband 17 may be a multi-piece waistband having multiple waistband adjustment means 19, such that the amount of trauma and movement that the patient undergoes in applying, adjusting, and changing device 11 is minimized. Frontal extension bands 21 extend from the front portion of waistband 17, along the pubic area of the patient, to catheter portion 13. Rear extension bands 23 extend from the rear portion of waistband 17, under the patient's groin area and on either side of the patient's scrotum 25, to catheter portion 13, as is shown in FIG. 2. It is preferred that frontal extension bands 19 and rear extension bands 21 be permanently attached to the exterior of waistband 17 to provide added comfort around the patient's waist. However, in some applications, it may be desirable for frontal extension bands 21 and/or rear extension bands 23 to be releasably and/or adjustably attached to waistband 17. Frontal extension bands 21 and rear extension bands 23 may include extension tabs 21a and 23a, respectively, which extend above waistband 17 to aid in adjusting the fit of device 11.

Each frontal extension band 21 adjustably and releasably attaches to catheter portion 13 with a conventional frontal extension adjustment means 27. It is preferred that frontal extension adjustment means 27 be a pair of parallel slots or grooves in catheter portion 13, but frontal extension adjustment means 27 may include tape, hooks, loops, buttons, or snaps. Each frontal extension adjustment means 27 is located near an upper edge 13a of catheter portion 13. In a similar fashion, each rear extension band 23 adjustably and releasably attaches to catheter portion 13 with a conventional rear extension adjustment means 29. It is preferred that rear extension adjustment means 29 be a pair of parallel slots or grooves in catheter portion 13, but rear extension adjustment means 29 may include tape, hooks, loops, buttons, or snaps. Each rear extension adjustment means 29 is located near a lower edge 13b of catheter portion 13. As is shown in FIG. 1, it is preferred that upper edge 13a of catheter portion 13 be longer across the patient than lower edge 13b of catheter portion 13. Indeed, catheter portion 13 may be close to a triangular shape. In this manner, catheter portion 13 may be removed and replaced without removing or replacing waistband portion 15.

Catheter portion 13 includes a base support portion 41 and an external condom portion 43. It is preferred that base support portion 41 and condom portion 43 be integral and formed of the same flexible material, such as latex, rubber, plastic, or any other suitable material for such medical applications. However, base support portion 41 and condom portion 43 may be releasably and sealingly coupled to each other. Condom portion 43 includes a shaft portion 43a, which conforms to a shaft 45 of the patient's penis; a bulbous portion 43b, which conforms to a head 47 of the patient's penis; and a coupling portion 43c, which is adapted to be releasably coupled to a conventional urinary drainage tube (not shown) and a conventional urinary drainage bag (not shown). Condom portion 43 functions in a similar manner to conventional external condom catheters, in that condom portion 43 fits snuggly around the patient's penis, such that urine and other fluids are expelled through coupling portion 43c, and do not leak onto the patient.

Referring now to FIG. 3 in the drawings, catheter portion 13 is shown in a cross-sectional view taken along III—III in FIG. 2. Base support portion 41 has a rear surface 45 that is preferably smooth and slightly concave. This shape allows catheter portion 13 to conform to the patient's pubic area. Base support portion 41 is generally of uniform thickness around the periphery, but gradually thickens toward the center of base support portion 41 to form a stiffened central portion 46. Condom portion 43 passes through a central aperture 47 in base support portion 41 and is integrally attached to base support portion 41 at an annular portion 49 at the rear of central portion 46. Central portion 46 supports the penis without unnecessary compression or restriction. It should be understood that condom portion 43 may attach to base support portion 41 at the front side of central portion 46 (see FIG. 3). By attaching condom portion 43 at the rear of base support portion 41, the additional length of condom portion 43 located within central portion 46 is available for snuggly fitting around the shaft 45 of the penis.

In operation, waistband 17 is placed around the patient's waist. Then, frontal extension bands 21 and rear extension bands 23 are adjusted and placed near the patient's pubic area. Then, coupling portion 43c is sealingly coupled to a conventional urinary drainage tube (not shown) and a conventional urinary drainage bag (not shown). Next, the patient's penis is inserted into condom portion 43 from the rear of base support portion 41 until head 47 is secured within bulbous portion 43b of condom portion 43. Shaft portion 43a of condom portion 43 snuggly fits around shaft 45 of the penis. It is preferred that aperture 47 through base support portion 41 have a large enough diameter so that the penis is not compressed or restricted. Then, frontal extension bands 21 and rear extension bands 23 are adjusted and releasably attached to catheter portion 13 with frontal extension adjustment means 27 and rear extension adjustment means 29, respectively. Thus assembled, device 11 will stay in place and not fall off of the patient's penis. As the patient passes fluid through the penis, the fluid is directed through coupling portion 43c and into the urinary drainage tube.

Referring now to FIG. 4 in the drawings, an alternate embodiment of the catheter portion according to the present invention is illustrated. In this embodiment, a catheter portion 50 includes a base support portion 51 and an external condom portion 53. Condom portion 53 includes a shaft portion 53a, a bulbous portion 53b, and a coupling portion 53c. Base support portion 51 has a rear surface 55 that is preferably smooth and slightly concave. This shape allows catheter portion 50 to conform to the patient's pubic area. Base support portion 51 is generally of uniform thickness around the periphery, but gradually thickens toward the center of base support portion 51 to form a stiffened central portion 56. An aperture 57 passes through central portion 56. Condom portion 53 is integrally attached to base support portion 51 at an annular portion 59 at the front of central portion 56. As in the preferred embodiment, central portion 56 supports the penis without unnecessary compression or restriction. Catheter portion 50 attaches to a strap portion (not shown) as described above with reference to the preferred embodiment.

Referring now to FIG. 5 in the drawings, another alternate embodiment of the condom catheter portion according to the present invention is illustrated. In this embodiment, a catheter portion 70 includes a base support portion 71 and an external condom portion 73. Condom portion 73 includes a shaft portion 73a, a bulbous portion 73b, and a coupling portion 73c. Base support portion 71 has a rear surface 75 that is preferably smooth and slightly concave. This shape allows catheter portion 70 to conform to the patient's pubic area. Base support portion 71 is generally of uniform thickness around the periphery, and retains this thickness toward the center of base support portion 71. A generally cylindrical central support portion 76 protrudes outward from the center of base support portion 71. An aperture 77 passes through the center of base support portion 71 and central support portion 76. In this embodiment, it is preferred that condom portion 73 is integrally attached to central support portion 76 at an annular portion 79 located at the front of central support portion 76. However, it should be understood that condom portion 73 may be integrally attached to central support portion 76 near the intersection of base support portion 71 and central support portion 76. In either case, central support portion 76 supports the penis without unnecessary compression or restriction. Catheter portion 70 attaches to a strap portion (not shown) as described above with reference to the preferred embodiment.

Referring now to FIGS. 6 and 7 in the drawings, an alternate embodiment of the male incontinence management device according to the present invention is illustrated. In this embodiment, a catheter portion 113 includes a base support portion 141 and a separate external condom portion 143. It is preferred that base support portion 141 and condom portion 143 be formed of a flexible material, such as latex, rubber, plastic, or any other suitable material for such medical applications. As with the preferred embodiment described above, catheter portion 113 is adjustably held in place by strap portion 15 which functions identically as described above (see FIGS. 1 and 2). As such, base support portion 141 includes frontal extension adjustment means 127 and rear extension adjustment means 129.

Condom portion 143 includes a shaft portion 143a, which conforms to the shaft of the patient's penis; a bulbous portion 143b, which conforms to the head of the patient's penis; and a coupling portion 143c, which is adapted to be releasably coupled to a conventional urinary drainage tube (not shown) and a conventional urinary drainage bag (not shown). It should be understood, that in this embodiment, condom portion 143 may be a conventional external condom catheter, or a novel condom catheter configured according to the specifications set forth herein. Condom portion 143 also includes stiffened, or reinforced, annular rib portion 143d. Rib portion 143d may be configured in a variety of ways. For example, rib portion 143d may form a circular ring, a rectangular ring, or any of a wide variety of cross-sectional shapes. This feature will be explained in more detail below.

Base support portion 141 has a rear surface 145 that is preferably smooth and slightly concave. This shape allows base support portion 141 to conform to the patient's pubic area. Base support portion 141 is generally of uniform thickness around the periphery, but gradually thickens toward the center of base support portion 141 to form a stiffened central portion 146. Central portion 146 supports the penis without unnecessary compression or restriction. A central aperture 147 passes through central portion 146 of base support portion 141.

As is best seen in FIG. 7, a condom catheter retaining means 151 is disposed on base support portion 141. Condom catheter retaining means 151 performs the function of sealingly coupling condom portion 143 to base support portion 141. In this multi-piece embodiment, it is preferred that condom catheter retaining means 151 is an annular groove disposed within rear surface 145 having a semicircular cross-sectional shape, as is shown in FIG. 6. Condom catheter retaining means 151 is configured to releasably receive and retain catheter portion 143. It should be understood that condom catheter retaining means 151 may take other shapes and configurations. In certain applications, it may be necessary for base support portion to include a separate retainer member (not shown), such as a stiff retaining ring, that couples and/or fastens condom portion 143 to base support portion 141.

In operation, rib portion 143d of catheter portion 143 is passed through aperture 147. By attaching condom portion 143 at the rear of base support portion 141, the additional length of condom portion 143 located within central portion 146 is available for snuggly fitting around the shaft of the penis. Rib portion 143d is then stretched over a tab portion 149 and installed into condom catheter retaining means 151. Rib portion 143d is typically stiffer and/or stronger than the other sections of catheter portion 143, usually due to being configured from more material than the other sections of catheter portion 143, or from being rolled up upon itself. This increased stiffness and/or strength ensures that catheter portion 143 stays coupled to base support portion 141 after installation. Once installed, a fluid tight seal is created between catheter portion 143 and base support portion 141 to ensure that the patient's urine and other fluids are passed to the urinary drainage bag (not shown). As necessary, catheter portion 143 may be easily removed and replaced with a new catheter portion 143. This may be done without removing strap portion 15.

Referring now to FIGS. 8A–8F in the drawings, a variety of embodiments of base support portion 141 are illustrated. In these figures, base support portion 141 is the same, except for the cross-sectional profile of condom catheter retaining means 151.

In FIG. 8A, a condom catheter retaining means 151a is configured as a groove having a generally circular cross-sectional area having a groove opening formed by a chord across the circle, i.e., a partially circular cross-section. Condom catheter retaining means 151a is well suited for catheter portions 143 having rib portions 143d for which the cross-sectional area generally forms the shape of a circle.

In FIG. 8B, a condom catheter retaining means 151b is configured as a groove having a generally rhombic cross-sectional area having a groove opening formed by the short parallel side of the rhombus. Condom catheter retaining means 151b is well suited for catheter portions 143 having rib portions 143d for which the cross-sectional area generally forms the shape of either a circle, square, or rectangle.

In FIG. 8C, a condom catheter retaining means 151c is configured as a groove having a generally rectangular cross-sectional area having a groove opening formed by a short side of the rectangle. Condom catheter retaining means 151c is well suited for catheter portions 143 having rib portions 143d for which the cross-sectional area generally forms the shape of either a square or rectangle.

In FIG. 8D, a condom catheter retaining means 151d is configured as a groove having a generally right triangular cross-sectional area having a groove opening formed by a chord across one corner of the right triangle. Condom catheter retaining means 151d is well suited for catheter portions 143 having rib portions 143d for which the cross-sectional area generally forms the shape of either a square, a rectangle, or a circle.

In FIG. 8E, a condom catheter retaining means 151e is configured as a groove having a generally inwardly pointing rectangular cross-sectional area having a groove opening formed by a chord across one corner of the short sides of the rectangle. Condom catheter retaining means 151e is well suited for catheter portions 143 having rib portions 143d for which the cross-sectional area generally forms the shape of either a square, a rectangle, or a circle.

In FIG. 8F, a condom catheter retaining means 151f is configured as a groove having a generally skewed circular cross-sectional area having a groove opening formed by a chord across the circle. Condom catheter retaining means 151f is well suited for catheter portions 143 having rib portions 143d for which the cross-sectional area generally forms the shape of a circle.

Although the present invention is shown in a limited number of forms, it is not limited to just these forms, but is amenable to various changes and modifications without departing from the spirit thereof.

I claim:

1. A male urinary incontinence management device comprising:

a base support portion having a periphery of generally uniform thickness, a front surface, a concave rear surface, a central portion that is stiffer than the periphery, and an aperture which passes through the central portion;

an external condom catheter portion integrally attached to the base support portion at the aperture such that the external condom catheter portion and the base support portion are of a single monolithic piece;

an adjustment means carried by the base support portion; and an adjustable strap portion releasably and adjustably attached to the base support portion at the adjustment means.

2. The male urinary incontinence management device comprising:

a base support having a periphery of generally uniform thickness, a front surface, a concave rear surface, a central portion that is stiffer than the periphery, and an aperture which passes through the central portion;

an external condom catheter portion integrally attached to the base support portion at the aperture;

an adjustment means carried by the base support portion;

an adjustable strap portion releasably and adjustably attached to the base support portion at the adjustment means;

an adjustable waistband;

at least one frontal extension band attached to the adjustable waistband, the at least one frontal extension band being adjustably and releasably attached to the base support portion; and at least one rear extension band attached to the adjustable waistband, the at least one rear extension band being adjustably and releasably attached to the base support portion.

3. The male urinary incontinence management device according to claim 1, wherein the base support portion increases in thickness from the periphery toward the aperture.

4. The male urinary incontinence management device according to claim 3, wherein the external condom catheter portion passes through the aperture and is integrally attached to the base support portion at the concave rear surface.

5. The male urinary incontinence management device according to claim 3, wherein the external condom catheter portion is integrally attached to the base support portion at the front surface.

6. A male urinary incontinence management device comprising:

a concave base support portion of generally uniform thickness, a,front surface, a rear surface, a central portion, and an aperture which passes through the central portion;

a generally cylindrical central support portion having a rear end and a front end, the rear end of the central support portion being integrally attached to the base support portion around the aperture;

an external condom catheter portion integrally attached to the central support portion such that the external condom catheter portion and the base support portion are of a single monolithic piece;

adjustment means carried by the base support portion; and an adjustable strap portion releasably and adjustably attached to the base support portion at the adjustment means.

7. A male urinary incontinence management device comprising:

a concave base support portion of generally uniform thickness, a front surface, a rear surface, a central portion, and an aperture which passes through the central portion;

a generally cylindrical central support portion having a rear end and a front end, the rear end of the central support portion being integrally attached to the base support portion around the aperture;

an external condom catheter portion integrally attached to the central support portion;

adjustment means carried by the base support portion;

an adjustable strap portion releasably and adjustably attached to the base support portion at the adjustment means;

an adjustable waistband;

at least one frontal extension band attached to the adjustable waistband, the at least one frontal extension band being adjustably and releasably attached to the base support portion; and at least one rear extension band attached to the adjustable waistband, the at least one rear extension band being adjustably and releasably attached to the base support portion.

8. The male urinary incontinence management device according to claim 6, wherein the external condom catheter portion passes through the central support portion and is integrally attached to the central support portion at the rear end.

9. The male urinary incontinence management device according to claim 6, wherein the external condom catheter portion is integrally attached to the central support portion at the front end.

10. A male urinary incontinence management device comprising:

a base support portion having a periphery of generally uniform thickness, a front surface, a concave rear surface, a central portion that is stiffer than the periphery, and an aperture which passes through the central portion;

an adjustment means carried by the base support portion;

an adjustable strap portion releasably and adjustably attached to the base support portion at the adjustment means;

an external condom catheter having an end rib portion, the external condom catheter passing through the aperture; and a condom catheter retaining means disposed on the rear surface, the condom catheter retaining means being integral with the rear surface and adapted to receive the end rib portion and sealingly attach the external condom catheter to the base support portion;

wherein the adjustable strap portion comprises an adjustable waistband;

at least one frontal extention band attached to the adjustable waistband, the at least one frontal extension band being adjustably and releasably attached to the base support portion; and at least one rear extension band attached to the adjustable waistband, the at least one rear extension band being adjustably and releasably attached to the base support portion.

11. The male urinary incontinence management device according to claim 10, wherein the end rib portion has a circular cross-section and the condom catheter retaining means is an annular groove having a generally semi-circular cross-section.

12. The male urinary incontinence management device according to claim 10, wherein the end rib portion has a circular cross-section and the condom catheter retaining means is an annular groove having a partially circular cross-section.

13. The male urinary incontinence management device according to claim 10, wherein the condom catheter retaining means is an annular groove having a partially triangular cross-section.

14. The male urinary incontinence management device according to claim 10, wherein the condom catheter retaining means is an annular groove having a rectangular cross-section.

15. The male urinary incontinence management device according to claim 10, wherein the condom catheter retaining means is an annular groove that is angled radially inward.

16. A male urinary incontinence management device for use with an existing external condom catheter having an end rib portion, the male urinary incontinence management device comprising:

a base support portion having a periphery of generally uniform thickness, a front surface, a concave rear surface, a central portion that is stiffer than the periphery, and an aperture which passes through the central portion;

an adjustment means carried by the base support portion;

an adjustable strap portion releasably and adjustably attached to the base support portion at the adjustment means; and a condom catheter retaining means disposed on the rear surface, the condom catheter retaining means being integral with the rear surface and adapted to receive the end rib portion and sealingly attach the external condom catheter to the base support portion;

wherein the adjustable strap portion comprises:

an adjustable waistband;

at least one frontal extension band attached to the adjustable waistband, the at least one frontal extension band being adjustably and releasably attached to the base support portion; and at least one rear extension band attached to the adjustable waistband, the at least one rear extension band being adjustably and releasably attached to the base support portion.

17. The male urinary incontinence management device according to claim 16, wherein the condom catheter retaining means is an annular groove having a partially circular cross-section.

18. The male urinary incontinence management device according to claim 16, wherein the condom catheter retaining means is an annular groove that is angled radially inward.

* * * * *